(12) United States Patent
Xu et al.

(10) Patent No.: US 9,061,270 B2
(45) Date of Patent: *Jun. 23, 2015

(54) CYCLOHEXANONE DEHYDROGENATION CATALYST AND PROCESS

(75) Inventors: Teng Xu, Houston, TX (US); Terry E. Helton, Bethlehem, PA (US); Jihad M. Dakka, Whitehouse Station, NJ (US); Tan-Jen Chen, Kingwood, TX (US); Sabato Miseo, Pittstown, NJ (US); Lorenzo C. Decaul, Langhorne, PA (US); Edward A. Lemon, Jr., Easton, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 90 days.

This patent is subject to a terminal disclaimer.

(21) Appl. No.: 13/520,467

(22) PCT Filed: Dec. 17, 2010

(86) PCT No.: PCT/US2010/061050
§ 371 (c)(1),
(2), (4) Date: Nov. 29, 2012

(87) PCT Pub. No.: WO2011/096999
PCT Pub. Date: Aug. 11, 2011

(65) Prior Publication Data
US 2013/0090499 A1  Apr. 11, 2013

Related U.S. Application Data

(60) Provisional application No. 61/301,799, filed on Feb. 5, 2010.

(30) Foreign Application Priority Data

Mar. 23, 2010  (EP) .................................... 10157371

(51) Int. Cl.
| | |
|---|---|
| C07C 37/08 | (2006.01) |
| C07C 37/00 | (2006.01) |
| B01J 29/04 | (2006.01) |
| B01J 21/00 | (2006.01) |
| B01J 23/58 | (2006.01) |
| B01J 21/08 | (2006.01) |
| B01J 37/02 | (2006.01) |
| B01J 37/12 | (2006.01) |
| C07C 2/74 | (2006.01) |
| C07C 37/06 | (2006.01) |
| C07C 45/53 | (2006.01) |
| C07C 407/00 | (2006.01) |
| C07C 37/07 | (2006.01) |

(52) U.S. Cl.
CPC *B01J 23/58* (2013.01); *B01J 21/08* (2013.01); *B01J 37/0205* (2013.01); *B01J 37/12* (2013.01); *C07C 2/74* (2013.01); *C07C 37/06* (2013.01); *C07C 37/08* (2013.01); *C07C 45/53* (2013.01); *C07C 407/00* (2013.01); *C07C 2101/14* (2013.01); *C07C 2529/70* (2013.01); *C07C 37/07* (2013.01)

(58) Field of Classification Search
USPC .................................... 568/798, 799; 585/430
See application file for complete search history.

(56) References Cited

U.S. PATENT DOCUMENTS

| | | | |
|---|---|---|---|
| 2,291,585 A | 7/1942 | Bartlett et al. | |
| 3,076,810 A | 2/1963 | Duggan et al. | |
| 3,194,843 A | 7/1965 | Silber et al. | |
| 3,211,668 A | 10/1965 | Yamamoto | |
| 3,238,120 A | 3/1966 | Sale | |
| 3,247,278 A | 4/1966 | Garwood et al. | |
| 3,358,044 A | 12/1967 | Russell et al. | |
| 3,442,958 A | 5/1969 | Choo | |
| 3,514,492 A | 5/1970 | Juguin et al. | |
| 3,519,575 A | 7/1970 | Bozik et al. | |
| 3,534,110 A * | 10/1970 | Le Page et al. | ............... 568/799 |
| 3,534,116 A | 10/1970 | Fuller | |
| 3,580,970 A | 5/1971 | Swift | |
| 3,691,102 A | 9/1972 | Swift | |
| 3,775,487 A | 11/1973 | Isbitsky, Jr. et al. | |
| 3,843,560 A | 10/1974 | Hayes | |
| 3,856,661 A | 12/1974 | Sugier et al. | |

(Continued)

FOREIGN PATENT DOCUMENTS

| | | |
|---|---|---|
| DE | 100 18 724 | 10/2001 |
| EP | 0 316 142 | 5/1989 |

(Continued)

OTHER PUBLICATIONS

Arends et al., "Selective Catalytic Oxidation of Cyclohexylbenzene to Cyclohexylbenzene-1-Hydroperoxide: A Coproduct-Free Route to Phenol" Tetrahedron, 2002, vol. 58, pp. 9055-9061.

(Continued)

*Primary Examiner* — Paul A Zucker
*Assistant Examiner* — Mark Luderer
(74) *Attorney, Agent, or Firm* — Siwen Chen; Stephen A. Baehl

(57) ABSTRACT

A catalyst composition comprising: (i) a support; (ii) a first component comprising at least one metal component selected from Group 1 and Group 2 of the Periodic Table of Elements; and (iii) a second component comprising at least one metal component selected from Groups 6 to 10 of the Periodic Table of Elements, wherein the catalyst composition exhibits an oxygen chemisorption of greater than 50%.

19 Claims, 1 Drawing Sheet

(56) References Cited

U.S. PATENT DOCUMENTS

| | | |
|---|---|---|
| 3,962,362 A | 6/1976 | Suggitt et al. |
| 4,070,413 A | 1/1978 | Imai |
| 4,088,603 A | 5/1978 | Carter et al. |
| 4,162,267 A | 7/1979 | Fisher et al. |
| 4,167,456 A | 9/1979 | Murtha |
| 4,169,857 A | 10/1979 | Murtha |
| 4,258,268 A | 3/1981 | Bjornson |
| 4,328,372 A | 5/1982 | Wu |
| 4,417,076 A | 11/1983 | Rozovsky et al. |
| 4,418,237 A | 11/1983 | Imai |
| 4,434,299 A | 2/1984 | Chang et al. |
| 4,520,129 A | 5/1985 | Murtha |
| 4,788,371 A | 11/1988 | Imai |
| 4,929,762 A | 5/1990 | Matsunaga et al. |
| 4,933,507 A | 6/1990 | Inoki et al. |
| 4,999,326 A | 3/1991 | Sikkenga et al. |
| 5,057,296 A | 10/1991 | Beck |
| 5,087,792 A | 2/1992 | Cottrell et al. |
| 5,102,643 A | 4/1992 | Kresge et al. |
| 5,180,871 A | 1/1993 | Matsunaga et al. |
| 5,256,348 A | 10/1993 | Waller |
| 5,292,960 A | 3/1994 | Meier et al. |
| 5,310,713 A | 5/1994 | Kojima et al. |
| 5,319,148 A | 6/1994 | Karcher et al. |
| 5,395,976 A | 3/1995 | Scharschmidt et al. |
| 5,569,635 A | 10/1996 | Moy et al. |
| 6,037,513 A | 3/2000 | Chang et al. |
| 6,376,422 B1 | 4/2002 | McNabb et al. |
| 6,417,135 B1 | 7/2002 | Dyroff |
| 6,579,821 B1 | 6/2003 | Ginosar et al. |
| 6,916,756 B2 | 7/2005 | Schindler et al. |
| 7,115,538 B2 | 10/2006 | Buchanan et al. |
| 7,256,149 B2 | 8/2007 | Grey et al. |
| 7,285,512 B2 | 10/2007 | Bai et al. |
| 7,285,685 B2 | 10/2007 | Walsdorff et al. |
| 7,396,798 B2 | 7/2008 | Ma et al. |
| 7,538,066 B2 | 5/2009 | Soled et al. |
| 2003/0083527 A1 | 5/2003 | Kuhnle et al. |
| 2004/0110630 A1 | 6/2004 | Schmidt et al. |
| 2006/0137817 A1 | 6/2006 | Ma et al. |
| 2007/0032681 A1 | 2/2007 | Walsdorff et al. |
| 2008/0039315 A1 | 2/2008 | Ma et al. |
| 2009/0215612 A1 | 8/2009 | McCarthy et al. |
| 2010/0075842 A1 | 3/2010 | Han et al. |
| 2011/0037022 A1 | 2/2011 | Dakka et al. |

FOREIGN PATENT DOCUMENTS

| | | | |
|---|---|---|---|
| EP | 0 328 507 | | 8/1989 |
| EP | 1050339 | * | 8/2000 ............... B01J 23/58 |
| EP | 1 050 339 | | 11/2000 |
| EP | 1 288 188 | | 3/2003 |
| EP | 1 430 949 | | 6/2004 |
| FR | 1 509 921 | | 1/1968 |
| FR | 1 541 720 | | 10/1968 |
| GB | 514 587 | | 11/1939 |
| GB | 986931 | | 3/1965 |
| GB | 1013715 | | 12/1965 |
| JP | 58 067636 | | 4/1983 |
| JP | 06-263668 | | 9/1994 |
| JP | 07-188082 | | 7/1995 |
| JP | 2637812 | | 8/1997 |
| JP | 2007-269522 | | 10/2007 |
| WO | 91/06616 | | 5/1991 |
| WO | 00/67902 | | 11/2000 |
| WO | 01/15803 | | 3/2001 |
| WO | 01/74767 | | 10/2001 |
| WO | 2007/009904 | | 1/2007 |
| WO | 2008/128638 | | 10/2008 |
| WO | 2009/131769 | | 10/2009 |
| WO | WO2009/131769 | * | 10/2009 ............... C07C 2/74 |
| WO | 2009/134514 | | 11/2009 |
| WO | 2010/024975 | | 3/2010 |

OTHER PUBLICATIONS

Borade et al., "Selective Dehydrogenation of Cyclohexene to Benzene using Pd-Exchanged α-Zirconium Phosphate", Catalysis Letters, 1997, vol. 45, pp. 233-235.

Cesar et al., "Stability and Selectivity of Bimetallic Cu-Co/SiO2 Catalysts for Cyclohexanol Dehydrogenation", Applied Catalysis A: General, vol. 176, No. 2, pp. 205-212.

Chen et al., "Nonoxidative Dehydrogenation of Cyclohexanol over Copper-Iron Binary Oxides", Applied Catalysis A: General, vol. 83, No. 2, pp. 201-211.

Corma, "From Microporous to Mesoporous Molecular Sieve Materials and Their Use in Catalysis", Chem. Rev., 1997, vol. 97, pp. 2373-2419.

Dobrovolszky et al., "Catalytic Transformations of Cyclohexanol on Group VIII Metal Catalysts", Journal of Catalysis, 1982, vol. 74, No. 1, pp. 31-43.

Fridman et al., "Dehydrogenation of Cyclohexanol on Copper-Containing Ctalysts:I. The Influence of the Oxidation State of Copper on the Activity of Copper Sites", Journal of Catalysis, vol. 111, No. 1, pp. 20-30.

Fridman et al., "Dehydrogenation of Cyclohexanol Over Copper-Zinc Catalysts", Neftekhimiya, vol. 29, No. 1, pp. 48-51-English Abstract Only.

Kamiguchi et al., "Catalytic Hydrodehydration of Cyclohexanone, Hydrogenation of 2-Cyclohexen-1-one, and Dehydrogenation of Cyclohexene over a Mo Chloride Cluster with an Octahedral Metal Framework", Journal of Cluster Science, 2005, vol. 16, No. 1, pp. 77-91.

Lezanska et al., "Characterization of Cr-MCM-41 and A1, Cr-MCM-14 Mesoporous Catalyst for Gas-Phase Oxidative Dehydrogenation of Cyclohexane", J. Phys. Chem. C., 2007, vol. 111, pp. 1830-1839.

Masai et al., "Dehydrogenation and Hydrogenation Activity of Palladium-Tin-Silica and Nickel-Tin-Silica", Journal of Catalysis, 1977, vol. 50, No. 3, pp. 419-428.

Masai et al., "Dehydrogenation Activity of Nickel-Tin-Silica Catalyst", Journal of Catalysis, 1975, vol. 38, pp. 128-134.

Milczanowski et al., "Catalytic Dehydrogenation of Cyclohexanone to Phenol", PrZEMYSL Cheniczny, 1978, vol. 57, No. 3, pp. 129-130-English Abstract Only.

Nikiforova et al., "Dehydrogenation of Cyclohexanol over Copper Supported on Magnesia", Neftekhimiya, 1973, vol. 78, No. 4, pp. 475-480.

Paal et al., "A Radiotracer Investigation of Transformations of Cyclohexanol in the Presence of a Nickel Powder Catalyst", Z Phys Chem, 1974, vol. 91, No. 1-4, pp. 54-66.

Saito et al. "Performance of activity test on supported Pd catalysts for dehydrogenation of cyclohexanone to phenol (effect of supports on activity)", Ibaraki Kogyo Koto Senmon Gakko Kenkyu Iho, 1995, vol. 30, pp. 39-46-English Abstract Only.

Samolada et al., "Catalyst Evaluation for Catalytic Biomass Pyrolysis", Energy & Fuels, 2000, vol. 14, pp. 1161-1167.

Solsona et al., "Vanadium Oxide Supported on Mesoporous MCM-41 as Selective Catalyst in the Oxidative Dehydrogenation of Alkanes", Journal of Catalysis, 2001, vol. 203, pp. 443-452.

Spieker et al., "Experimental Investigation and Modeling of Platinum Adsorption onto Ion-moded Silica and Alumina", Studies in Surface Science and Catalysis, 2000, vol. 130, pp. 203-208.

Swift et al., "Metallic Phases and Activites of Nickel-Tin-Silica Catalysts Dehydrogenation of Cyclohexanone, Cyclohexanol, and Cyclohexane", Journal of Catalysis, 1968, vol. 12, pp. 5-14.

Waligora et al., "Catalytic Dehydrogenation of Mixture of Cyclohexanol and Cyclohexanon to Phenol", Prace Chemiczne, 1982, vol. 27, pp. 93-99-English Abstract Only.

* cited by examiner

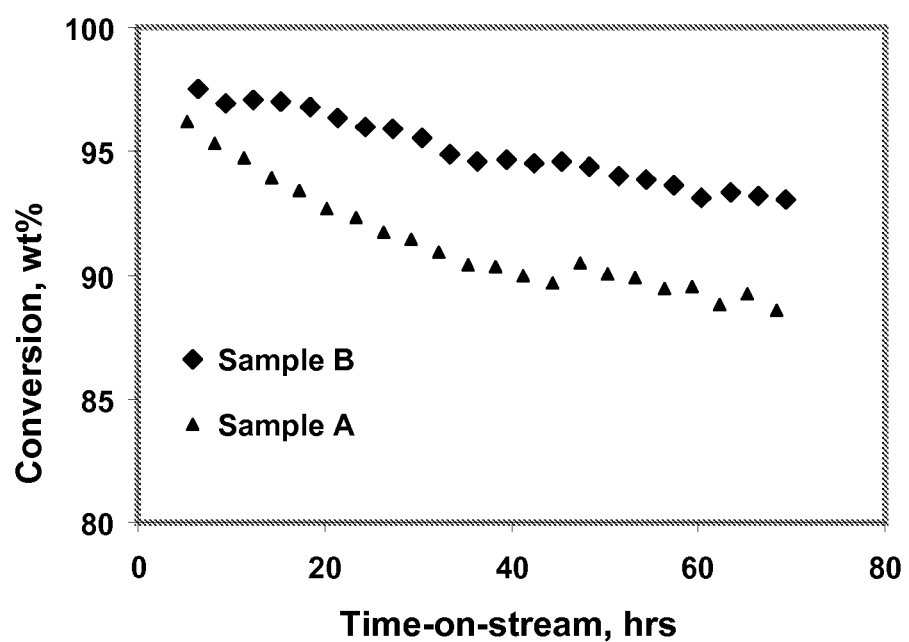

CYCLOHEXANONE DEHYDROGENATION CATALYST AND PROCESS

PRIORITY CLAIM

This patent application is a National Stage Application of International Application No. PCT/US2010/061050 filed Dec. 17, 2010, which claims priority to U.S. Provisional Application Ser. No. 61/301,799, filed Feb. 5, 2010; and European Application No. 10157371.5 filed Mar. 23, 2010, the disclosures of which are fully incorporated herein by their reference.

CROSS REFERENCE TO RELATED APPLICATIONS

This patent application is related to U.S. Provisional Application Ser. No. 61/301,780, filed Feb. 5, 2010; U.S. Provisional Application Ser. No. 61/301,786, filed Feb. 5, 2010, 2010; U.S. Provisional Application Ser. No. 61/301,794, filed Feb. 5, 2010, the disclosures of which are fully incorporated herein by their reference.

FIELD

The present invention relates to a dehydrogenation catalyst, its synthesis and its use in the dehydrogenation of a dehydrogenatable hydrocarbon.

BACKGROUND

Various dehydrogenation processes have been proposed to dehydrogenate dehydrogenatable hydrocarbons such as cyclohexanone and cyclohexane. For example, these dehydrogenation processes have been used to convert at least a portion of cyclohexanone into phenol.

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone.

Other known routes for the production of phenol involve the direct oxidation of benzene, the oxidation of toluene, and the oxidation of s-butylbenzene wherein methyl ethyl ketone is co-produced with phenol in lieu of acetone produced in the Hock process.

Additionally, phenol can be produced by the oxidation of cyclohexylbenzene to cyclohexylbenzene hydroperoxide wherein cyclohexanone is co-produced with phenol in lieu of acetone produced in the Hock process. A producer using this process may desire to dehydrogenate at least a portion of the cyclohexanone produced into the additional phenol depending on market conditions.

For example, U.S. Pat. No. 3,534,110 discloses a process for the catalytic dehydrogenation of cyclohexanone and/or cyclohexanol to phenol over a catalyst comprising platinum and preferably iridium on a silica support. The catalyst also contains 0.5 to 3 wt % of an alkali or alkaline earth metal compound, which, according to column 3, lines 43 to 49, should be incorporated after addition of the platinum since otherwise the resulting catalyst composition has inferior activity, selectivity and life.

In addition, U.S. Pat. No. 4,933,507 discloses that phenol can be produced by dehydrogenating cyclohexenone through a vapor-phase reaction in the presence of hydrogen using a solid-phase catalyst having platinum and alkali metal carried on a support, such as silica, silica-alumina or alumina. The catalyst is prepared by first treating the support with an aqueous solution of platinic acid, etc., to have platinum chloride carried on the support, then treating the support to have an alkali metal compound such as $K_2CO_3$ supported thereon, and finally reducing the treated support. The content of alkali metal in the catalyst is preferably in the range of 0.5-2.0 weight % (wt %) in terms of $Na_2O$ based on the weight of the support and in the range of 0.2-3.0 wt % in terms of $K_2CO_3$ based on the weight of the platinum.

U.S. Pat. No. 7,285,685 discloses a process for the dehydrogenation of a saturated carbonyl compound, such as cyclohexanone, in the gas phase over a heterogeneous dehydrogenation catalyst comprising platinum and/or palladium and tin on an oxidic support, such as zirconium dioxide and/or silicon dioxide. In addition, the dehydrogenation catalyst can further comprise one or more elements of Groups 1 and/or 2, preferably potassium and/or cesium, which are added to the catalyst as aqueous solutions of compounds which can be converted into the corresponding oxides by calcination. In the only catalyst preparation example, an aqueous solution containing $CsNO_3$ and $KNO_3$ is added to a silica/titania support after the support has been impregnated with a solution of $SnCl_2.2H_2O$ and $H_2PtCl_6.6H_2O$ in ethanol, then dried at 100° C. for 15 hours and calcined at 560° C. for 3 hours.

One problem that has been encountered in the use of supported noble metal catalysts in the dehydrogenation of cyclohexanone is that the activity of the noble metal decreases fairly rapidly unless the metal is well dispersed on the support. However, a typical catalyst produced by directly impregnating a noble metal onto a support tends to result in poor metal dispersion because of non-uniform metal particle sizes. Thus, the resultant catalyst generally deactivates rapidly and so requires frequent reactivation or replacement. Given the high cost of noble metals and the loss in production time involved with frequent reactivation, there is, therefore, a need for a cyclohexanone dehydrogenation catalyst having improved resistance to deactivation.

According to the present invention, it has now been found that an oxide-supported, metal-containing cyclohexanone dehydrogenation catalyst having improved stability and activity, as measured by its unique oxygen chemisorptions properties, can be obtained if, prior to addition of the dehydrogenation metal, the oxide support is treated with a Group 1 or Group 2 metal promoter (i.e., alkali metal or alkaline earth metals) and then calcined under controlled conditions.

SUMMARY

In one aspect, the invention resides in a catalyst composition comprising: (i) a support; (ii) a first component wherein the first component is at least one metal component selected from Group 1 and Group 2 of the Periodic Table of Elements wherein the first component is present in an amount of at least 0.1 wt %; and (iii) a second component comprising at least one metal component selected from Groups 6 to 10 of the Periodic Table of Elements; wherein the catalyst composition exhibits an oxygen chemisorption of greater than 50%.

Conveniently, the catalyst composition exhibits an oxygen chemisorption of greater than 60%, such as greater than 70%.

Conveniently, the support is selected from the group consisting of silica, a silicate, an aluminosilicate, zirconia, carbon, and carbon nanotubes, and preferably comprises silica.

In one embodiment, the first component comprises at least one metal component selected from potassium, cesium and rubidium.

In one embodiment, the first component comprises at least one metal component comprising potassium.

Conveniently, the second component comprises at least one metal component selected from Group 10 of the Periodic Table of Elements.

Conveniently, the second component comprises at least one metal component selected from platinum and palladium, and preferably the at least one metal component comprises platinum.

Typically, the catalyst composition is capable of dehydrogenating cyclohexanone at a conversion of 95% or more.

In a further aspect, the invention resides in a method for preparing a catalyst composition, the method comprising:
(a) treating a support with a first component comprising at least one metal component selected from Group 1 and Group 2 of the Periodic Table of Elements;
(b) calcining the treated support at a temperature of about 100° C. to about 700° C.; and
(c) impregnating the support with a second component comprising at least one metal component selected from Groups 6 to 10 of the Periodic Table of Elements,
wherein the impregnating (c) is effected after or at the same time as the treating (a).

Conveniently, the calcining (b) is conducted in an oxygen-containing atmosphere.

In one embodiment, the impregnating (c) is effected after the treating (a) and the calcining (b) and the method further comprises:
(d) calcining the impregnated support at a temperature of about 100° C. to about 700° C.

Conveniently, the calcining (d) is conducted in an oxygen-containing atmosphere.

In yet a further aspect, the invention resides in a process of producing phenol by dehydrogenating cyclohexanone in the presence of the catalyst composition described herein.

BRIEF DESCRIPTION OF THE DRAWINGS

FIG. 1 is a graph comparing cyclohexanone conversion against time on stream for the 1% K/1% Pt/SiO$_2$ catalyst of Example 1 with that of the 1% Pt/1% K/SiO$_2$ catalyst of Example 2.

DETAILED DESCRIPTION

Described herein is a process for dehydrogenating at least one dehydrogenatable hydrocarbon such as cyclohexanone wherein the dehydrogenation catalyst support comprises a support material; a first component comprising at least one metal component selected from Group 1 and Group 2 of the Periodic Table of Elements; and a second component comprising at least one metal component selected from Groups 6 to 10 of the Periodic Table of Elements. Specifically, this dehydrogenation catalyst can be utilized in a phenol process wherein cyclohexanone is co-produced with phenol by allowing at least a portion of the co-produced cyclohexanone to be converted to additional phenol. In the phenol process wherein cyclohexanone is co-produced, cyclohexylbenzene, generally produced by the catalytic hydroalkylation of benzene, is oxidized to produce cyclohexylbenzene hydroperoxide and then the cyclohexylbenzene hydroperoxide is cleaved to produce an effluent stream comprising phenol and cyclohexanone in substantially equimolar amounts. At least a portion of the effluent is then fed to a dehydrogenation reaction zone, where the effluent stream portion is contacted with a dehydrogenation catalyst so as to convert the cyclohexanone in the effluent portion into additional phenol and into hydrogen, which can be recycled to the benzene hydroalkylation step.

As used herein, the numbering scheme for the Periodic Table Groups is as disclosed in Chemical and Engineering News, Vol. 63(5), p. 27 (1985).

Dehydrogenation Catalyst and Process

The dehydrogenation process may be used to dehydrogenate any dehydrogenatable hydrocarbon such as an alicyclic compound. "Dehydrogenatable hydrocarbon" refers to all classes of hydrocarbons containing saturated carbon bonds which have the potential for forming one or more unsaturated bonds through the process of dehydrogenation. "Alicyclic compounds" refers to saturated or unsaturated non-aromatic hydrocarbon ring systems containing from three to twenty ring carbon atoms wherein the hydrocarbon ring system may also have a side-chain or a functional group attached directly to or bound within the ring. Examples of alicyclic compounds include, without limitation, cyclopropane, cyclopentane, methyl cyclopentane, cyclobutane, cyclopentene, cyclodecane, cyclohexane, methylcyclohexane, cyclododecane, and six carbon ring alicyclic compounds such as cyclohexane. Other examples of alicyclic compounds include, without limitation, alicyclic ketones such as cyclohexanone and alicyclic alcohols such as cyclohexanol.

In one embodiment, at least a portion of the six carbon ring alicyclic compounds are dehydrogenated (or converted) to aromatic compounds such as benzene and phenol. For example, at least a portion of cyclohexanone may be dehydrogenated to phenol and at least a portion of cyclohexane may be dehydrogenated to benzene.

In another embodiment, at least a portion of the alicyclic compounds are (i) dehydrogenated to unsaturated compounds; (ii) rearranged to form other alicyclic compounds; or (iii) fragment to lighter hydrocarbons.

The novel catalyst employed in the cyclohexanone dehydrogenation reaction comprises: (i) a support; (ii) a first component; and (iii) a second component produced such that the catalyst exhibits an oxygen chemisorption of greater than 50%, preferably greater than 60% and more preferably greater than 70%.

Conveniently, the support employed in the dehydrogenation catalyst is selected from the group consisting of silica, a silicate, an aluminosilicate, zirconia, carbon, and carbon nanotubes, and preferably comprises silica. Impurities which can be present in the catalyst support (e.g., silica) are, for example, sodium salts such as sodium silicate which can be present from anywhere from 0.01 to 2 wt %.

In one embodiment, the dehydrogenation catalyst comprises a silica support having pore volumes and median pore diameters determined by the method of mercury intrusion porosimetry described by ASTM Standard Test D4284. The silica support may have surface areas as measured by ASTM D3663. In one embodiment, the pore volumes are in the range of from about 0.2 cc/gram to about 3.0 cc/gram. The median pore diameters are in the range from about 10 angstroms to about 2000 angstroms or from 20 angstroms to 500 angstroms; and the surface areas (m2/gram) are in the range from 10 to 1000 m2/gram or from 20 to 500 m2/gram.

Generally, the catalyst comprises a first component comprising at least one metal component selected from Group 1 and Group 2 of the Periodic Table of Elements, such that the first component may comprise any combination or mixture of metal components selected from Groups 1 and 2 of the Periodic Table of Elements. Typically, the first component is present in an amount of at least 0.1 wt %, at least 0.2 wt %, at least 0.3 wt %, at least 0.4 wt %, at least 0.5 wt %, at least 0.6 wt %, at least 0.7 wt %, at least 0.8 wt %, at least 0.9 wt %, and at least 1.0 wt %. In one embodiment, the first component comprises at least one metal component selected from Group 1 of the Periodic Table of Elements, such as potassium, cesium and rubidium; preferably potassium and potassium compounds. In another embodiment, the first component comprises at least one metal component selected from Group 1 of the Periodic Table of Elements. In still another embodiment, the first component comprises at least one metal component selected from Group 2 of the Periodic Table of Elements such as beryllium, calcium, magnesium, strontium, barium and radium; preferably calcium and magnesium. Typically, the first component is present in an amount between about 0.1 and about 5 wt % of the catalyst or between about 0.2 and about 4 wt % of the catalyst or between about 0.3 and about 3 wt % of the catalyst.

In addition, the catalyst comprises a second component comprising at least one metal component selected from Groups 6 to 10 of the Periodic Table of Elements, such as platinum and palladium such that the second component may comprise any combination or mixture of metal components selected from Groups 6 to 10 of the Periodic Table of Elements. In another embodiment, the second component comprises at least one metal component selected from Group 10 of the Periodic Table of Elements. Typically, the second component is present in an amount between about 0.1 and about 10 wt % of the catalyst.

The term "metal component" is used herein to include a metal compound that may not be purely the elemental metal, but could, for example, be at least partly in another form, such as an oxide, hydride or sulfide form. The weight % (wt %) of the metal component is herein defined as being measured as the metal present based on the total weight of the catalyst composition irrespective of the form in which the metal component is present.

The dehydrogenation catalyst is produced by initially treating the support, such as by impregnation, with a solution of the first component, such as an aqueous solution of potassium carbonate. After drying, the treated support is calcined, normally in an oxygen-containing atmosphere, such as air, at a temperature of about 100° C. to about 700° C. for a time of about 0.5 to about 50 hours. The calcined support is then treated, again typically by impregnation, with a solution of the second component or a precursor thereof.

Optionally, the second component may be impregnated into the support with the aid of at least one organic dispersant. The organic dispersant may help to increase the metal dispersion of the first component. The at least one organic dispersant may be used to increase the metal dispersion of the second component with or without the impregnation of the first component into the support. The at least one organic dispersant is selected from an amino alcohol and an amino acid, such as arginine. Generally, the organic dispersant is present in an amount between about 1 and about 20 wt % of the solution.

After treatment with the second component, the support is again dried and calcined, normally in an oxygen-containing atmosphere, such as air, at a temperature of about 100° C. to about 700° C. for a time of about 0.5 to about 50 hours.

In one embodiment, after treatment with the second component, the support is again dried and calcined, normally in an oxygen-containing atmosphere, such as air, at a temperature of about 100° C. to about 600° C. for a time of about 0.5 to about 50 hours.

After application of each of the first component and second component to the support, the support is preferably heated at a temperature of about 100° C. to about 700° C., for example about 200° C. to about 500° C., such as about 300° C. to about 450° C., for a time of about 0.5 to about 50 hours, such as about 1 to about 10 hours. In addition to removing any liquid carrier and dispersant used to apply the metal component(s) to the support, the heating is believed to assist in bonding the metal to the support and thereby improve the stability of the final catalyst. The heating is preferably conducted in an oxidizing atmosphere, such as air, although a reducing atmosphere, such as hydrogen, can also be employed.

Preferably, the temperature of the calcination after treatment with the first and second component is from about 100° C. to about 600° C.; from about 150° C. to about 550° C.; from about 200° C. to about 500° C., from about 250° C. to about 450° C., and from about 275° C. to about 425° C. In other embodiments, the calcination temperature lower limit may be about 100° C., about 150° C., about 200° C., about 225° C., about 250° C., about 275° C., about 300° C., and about 325° C.; and the upper limit temperature may be about 600° C., about 550° C., about 500° C., about 475° C., about 450° C., about 425° C., about 400° C., about 375° C., and about 350° C. with ranges from any lower limit to any upper limit being contemplated. Preferably, the calcination period is for a time of about 0.5 to about 50 hours.

Preferably, the majority of the calcination after treatment with the first and second component occurs from about 100° C. to about 600° C.; from about 150° C. to about 550° C.; from about 200° C. to about 500° C., from about 250° C. to about 450° C., and from about 275° C. to about 425° C. In other embodiments, the calcination temperature lower limit wherein the majority of the calcination occurs may be about 100° C., about 150° C., about 200° C., about 225° C., about 250° C., about 275° C., about 300° C., and about 325° C.; and the upper limit temperature may be about 600° C., about 550° C., about 500° C., about 475° C., about 450° C., about 425° C., about 400° C., about 375° C., and about 350° C. with ranges from any lower limit to any upper limit being contemplated. Preferably, the calcination period is for a time of about 0.5 to about 50 hours.

In an alternative embodiment, the dehydrogenation catalyst is produced by initially treating the support, such as by impregnation, with a solution containing both the first component and the second component or a precursor thereof, optionally together with at least one organic dispersant selected from an amino alcohol and an amino acid, such as arginine. In this case, after drying, a single calcination procedure, normally in an oxygen-containing atmosphere, such as air, at a temperature of about 100° C. to about 700° C. for a time of about 0.5 to about 50 hours, is used to produce the finished catalyst.

Suitable conditions for the dehydrogenation step include a temperature of about 250° C. to about 750° C., a pressure of about atmospheric to about 500 psi-gauge (psig) [100 to 3447 kPa-gauge (kPag)], a weight hourly space velocity of about 0.2 to 50 hr$^{-1}$, and a hydrogen to cyclohexanone-containing feed molar ratio of about 0 to about 20.

Preferably, the temperature of the dehydrogenation process is from about 300° C. to about 750° C.; from about 350° C. to about 650° C.; from about 400° C. to about 550° C., from about 450° C. to about 550° C., and from about 400° C. to about 500° C. In other embodiments, the temperature lower limit may be about 350° C., about 400° C., about 430° C., about 440° C., about 450° C., about 460° C., about 470° C., about 480° C., and about 490° C.; and the upper limit temperature may be about 500° C., about 510° C., about 520° C., about 530° C., about 540° C., about 550° C., about 600° C., about 650° C., about 700° C., and about 750° C. with ranges from any lower limit to any upper limit being contemplated. In still other embodiments, the temperature lower limit may be about 500° C., about 510° C., about 520° C., about 530° C., about 540° C., and about 550° C.; and the upper limit temperature may be about 560° C., about 570° C., about 580° C., about 590° C., about 600° C., about 650° C., about 700° C., and about 750° C. with ranges from any lower limit to any upper limit being contemplated.

Preferably, the pressure of the dehydrogenation process is from 0 to about 300 psig (0 to 2068 kPag), 50 to 300 psig (345 to 2068 kPag), from 60 to 300 psig (414 to 2068 kPag), from 70 to 300 psig (482 to 2068 kPag), from 80 to 300 psig (552 to 2068 kPag), from 90 to 300 psig (621 to 2068 kPag), and from 100 to 300 psig (689 to 2068 kPag). In other embodiments, the temperature lower limit may be 50 psig (345 kPag), 60 psig (414 kPag), 70 psig (482 kPag), 80 psig (552 kPag), 90 psig (621 kPa), and 100 psig (689 kPag); and the upper limit temperature may be 125 psig (862 kPag), 150 psig (1034 kPag), 175 psig (1207 kPag), 200 psig (1379 kPag), 250 psig (1724 kPag), 300 psig (2068 kPag), 400 psig (2758 kPag), and 500 psig (3447 kPag) with ranges from any lower limit to any upper limit being contemplated. In still other embodiments, the temperature lower limit may be 150 psig (1034 kPag), 160 psig (1103 kPag), 170 psig (1172 kPag), 180 psig (1241 kPag), 190 psig (1310 kPag), and 200 psig (1379 kPag); and the upper limit temperature may be 250 psig (1724 kPag), 300 psig (2068 kPag), 400 psig (2758 kPag), and 500 psig (3447 kPag) with ranges from any lower limit to any upper limit being contemplated.

The reactor configuration used for the dehydrogenation process generally comprises one or more fixed bed reactors containing a solid catalyst with a dehydrogenation function. Per-pass conversion of cyclohexanone using the present catalyst is greater than 70%, and typically at least 95%. Provision can be made for the endothermic heat of reaction, preferably by multiple adiabatic beds with interstage heat exchangers. The temperature of the reaction stream drops across each catalyst bed, and then is raised by the heat exchangers. Preferably, 3 to 5 beds are used, with a temperature drop of about 30° C. to about 100° C. across each bed. Preferably the last bed in the series runs at a higher exit temperature than the first bed in the series.

Cyclohexanone and phenol produce an azeotropic mixture composed of 28 wt % cyclohexanone and 72 wt % phenol, so that any attempt to separate cyclohexanone from the cleavage effluent by simple distillation results in this azeotropic mixture. However, the efficiency of the separation can be enhanced by conducting the distillation under at least partial vacuum, typically at below 101 kPa. Moreover, extractive distillation processes are known for separating cyclohexanone and phenol, see for example, U.S. Pat. Nos. 4,021,490; 4,019,965; 4,115,207; 4,115,204; 4,115,206; 4,201,632; 4,230,638; 4,167,456; 4,115,205; and 4,016,049. Nevertheless, phenol/cyclohexanone separation remains a costly process, so that in one embodiment, the feed to the dehydrogenation step has the same composition as the cleavage effluent, thereby avoiding the need for an initial expensive separation step.

In another embodiment, the cleavage effluent is subjected to one or more separation processes to recover or remove one or more components of the effluent prior to dehydrogenation. In particular, the cleavage effluent is conveniently subjected to at least a first separation step to recover some or all of the phenol from the effluent, typically so that the effluent stream fed to the dehydrogenation reaction contains less than 50 wt %, for example less than 30 wt %, such as less than 1 wt %, phenol. The first separation step is conveniently effected by vacuum distillation and the same, or additional vacuum distillation steps, can be used to remove components boiling below 155° C. (as measured at 101 kPa), such as benzene and cyclohexene, and/or components boiling above 185° C. (as measured at 101 kPa), such as 2-phenyl phenol and diphenyl ether, prior to feeding the effluent stream to the dehydrogenation reaction.

By employing the present dehydrogenation process, substantially all the cyclohexanone in the cyclohexylbenzene hydroperoxide cleavage effluent can be converted to phenol. In practice, however, depending on market conditions, there is likely to be a significant demand for cyclohexanone product. This can be readily met by using the present process by reliance on the reversible nature of the reaction (2), namely by hydrogenating at least some of the phenol back to cyclohexanone. This can readily be achieved by, for example, contacting the phenol with hydrogen in the presence of a hydrogenation catalyst, such as platinum or palladium, under conditions including a temperature of about 20° C. to about 250° C., a pressure of about 101 kPa to about 10000 kPa and a hydrogen to phenol molar ratio of about 1:1 to about 100:1.

Production of Cyclohexylbenzene

The cyclohexylbenzene employed in the present process can be produced by any conventional technique, including alkylation of benzene with cyclohexene in the presence of an acid catalyst, such as zeolite beta or an MCM-22 family molecular sieve, or by oxidative coupling of benzene to biphenyl followed by hydrogenation of the biphenyl. However, in practice, the cyclohexylbenzene is generally produced by contacting benzene with hydrogen under hydroalkylation conditions in the presence of a hydroalkylation catalyst whereby the benzene undergoes the following reaction (1) to produce cyclohexylbenzene (CHB):

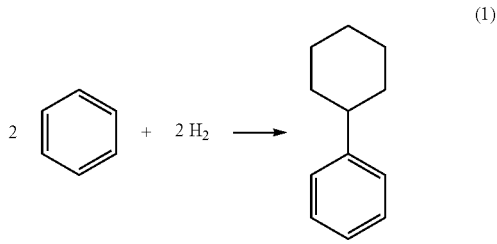 [SMILES: c1ccccc1 ; c1ccc(C2CCCCC2)cc1]

(1)

Details of such a process for producing cyclohexylbenzene can be found in paragraphs [0027] through [0038] of WO 2009/131769, the disclosure of which is hereby incorporated by reference.

Cyclohexylbenzene Oxidation

In order to convert the cyclohexylbenzene into phenol and cyclohexanone, the cyclohexylbenzene is initially oxidized to the corresponding hydroperoxide. This is accomplished by introducing an oxygen-containing gas, such as air, into a liquid phase containing the cyclohexylbenzene. Unlike cumene, atmospheric air oxidation of cyclohexylbenzene in the absence of a catalyst is very slow and hence the oxidation is normally conducted in the presence of a catalyst.

Details of such a process for producing cyclohexylbenzene can be found in paragraphs [0048] through [0055] of WO 2009/131769, the disclosure of which is hereby incorporated by reference.

Hydroperoxide Cleavage

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of about 20° C. to about 150° C., such as about 40° C. to about 120° C., a pressure of about 50 to about 2,500 kPa, such as about 100 to about 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction is conveniently conducted in a catalytic distillation unit.

Details of such a process for hydroperoxide cleavage can be found in paragraphs [0056] through [0075] of WO 2009/131769, the disclosure of which is hereby incorporated by reference.

Treatment of Cleavage Effluent

The effluent from the cleavage reaction comprises phenol and cyclohexanone in substantially equimolar amounts. The present process provides an advantageous route to increasing the amount of phenol produced from the original benzene feed by contacting at least a portion of the cleavage effluent with a dehydrogenation catalyst so as to convert some or all of the cyclohexanone in the effluent into additional phenol according to the reaction (2):

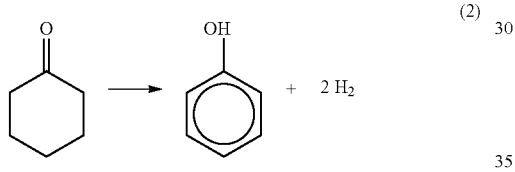

(2)

In one embodiment, the dehydrogenation catalyst and process described herein may be used in reaction (2).

Cyclohexanone and phenol produce an azeotropic mixture composed of 28 wt % cyclohexanone and 72 wt % phenol, so that any attempt to separate the effluent from the cyclohexylbenzene hydroperoxide cleavage step by simple distillation results in this azeotropic mixture. However, the efficiency of the separation can be enhanced by conducting the distillation under at least partial vacuum, typically at below 101 kPa. Moreover, extractive distillation processes are known for separating cyclohexanone and phenol, see for example, U.S. Pat. Nos. 4,021,490; 4,019,965; 4,115,207; 4,115,204; 4,115,206; 4,201,632; 4,230,638; 4,167,456; 4,115,205; and 4,016,049. Nevertheless, phenol/cyclohexanone separation remains a costly process, so that in one embodiment, the feed to the dehydrogenation step has the same composition as the cleavage effluent, thereby avoiding the need for an initial expensive separation step. Depending on the efficiency of the cyclohexanone dehydrogenation, the final product may contain substantially all phenol, thereby at least reducing the problem of separating the phenol from the cleavage effluent.

In another embodiment, the cleavage effluent is subjected to one or more separation processes to recover or remove one or more components of the effluent prior to dehydrogenation. In particular, the cleavage effluent is conveniently subjected to at least a first separation step to recover some or all of the phenol from the effluent, typically so that the effluent stream fed to the dehydrogenation reaction contains less than 50 wt %, for example, less than 30 wt %, such as less than 1 wt %, phenol. The first separation step is conveniently effected by vacuum distillation and the same, or additional vacuum distillation steps, can be used to remove components boiling below 155° C. (as measured at 101 kPa), such as benzene and cyclohexene, and/or components boiling above 185° C. (as measured at 101 kPa), such as 2-phenyl phenol and diphenyl ether, prior to feeding the effluent stream to the dehydrogenation reaction.

By employing the present dehydrogenation process, substantially all the cyclohexanone in the cyclohexylbenzene hydroperoxide cleavage effluent can be converted to phenol. In practice, however, depending on market conditions, there is likely to be a significant demand for cyclohexanone product. This can readily be met by using the present process by reliance on the reversible nature of the reaction (2), namely by hydrogenating at least some of the phenol back to cyclohexanone. This can readily be achieved by, for example, contacting the phenol with hydrogen in the presence of a hydrogenation catalyst, such as platinum or palladium, under conditions including a temperature of about 20° C. to about 250° C., a pressure of about 101 kPa to about 10000 kPa and a hydrogen to phenol molar ratio of about 1:1 to about 100:1.

Provided are one or more embodiments:

A. A process for the dehydrogenation of at least one dehydrogenatable hydrocarbon, the process comprising contacting a feed comprising at least one dehydrogenatable hydrocarbon with a catalyst comprising an inorganic oxide support, a first component comprising at least one metal component selected from Group 1 and Group 2 of the Periodic Table of Elements, and a second component comprising at least one metal component selected from Groups 6 to 10 of the Periodic Table of Elements and under dehydrogenation conditions effective to convert at least part of the at least one dehydrogenatable hydrocarbon in the feed, wherein the catalyst is produced by a method comprising:
  (a) treating the support with the first component;
  (b) calcining the treated support at a temperature of about 100° C. to about 700° C.;
  (c) impregnating the support with the second component; and
  (d) calcining the impregnated support at a temperature of about 100° C. to about 700° C.,
  wherein the impregnating (c) is effected after or at the same time as any treating of the support with the first component.

B. The process of embodiment A, wherein the inorganic support is selected from the group consisting of silica, a silicate, and an aluminosilicate.

C. The process of embodiment A and B, wherein the inorganic support comprises silica.

D. The process of any one of embodiments A to C, wherein the second component comprises at least one metal component selected from platinum and palladium.

E. The process of any one of embodiments A to D, wherein the first component comprises a metal component comprising potassium.

F. The process of any one of embodiments A to E, wherein the calcining (b) is conducted in an oxygen-containing atmosphere.

G. The process of any one of embodiments A to F, wherein the calcining (d) is conducted in an oxygen-containing atmosphere.

H. The process of any one of embodiments A to G, wherein the dehydrogenation conditions include a temperature of about 250° C. to about 500° C., a pressure of about 100 to about 3550 kPa, a weight hourly space velocity of about 0.2 to 50 $hr^{-1}$, and a hydrogen to cyclohexanone-containing feed molar ratio of about 2 to about 20.

I. A process for producing phenol from benzene, the process comprising:
 (i) contacting benzene and hydrogen with a catalyst under hydroalkylation conditions to produce cyclohexylbenzene;
 (ii) oxidizing at least a portion of the cyclohexylbenzene from the contacting (i) to produce cyclohexylbenzene hydroperoxide;
 (iii) converting at least a portion of the cyclohexylbenzene hydroperoxide from the oxidizing (ii) to produce an effluent stream comprising phenol and cyclohexanone; and
 (iv) contacting at least a portion of the effluent stream with a catalyst comprising an inorganic oxide support, a first component comprising at least one metal component selected from Group 1 and Group 2 of the Periodic Table of Elements, and a second component comprising at least one metal component selected from Groups 6 to 10 of the Periodic Table of Elements under dehydrogenation conditions effective to convert at least part of the cyclohexanone in the feed into phenol and hydrogen, wherein the catalyst is produced by a method comprising:
  (a) treating the support with the first component;
  (b) calcining the treated support at a temperature of about 100° C. to about 700° C.;
  (c) impregnating the support with a compound of the second component; and
  (d) calcining the impregnated support at a temperature of about 100° C. to about 700° C.,
 wherein the impregnating (c) is effected after or at the same time as any treating of the support with the first component.
J. The process of embodiment I, wherein the inorganic support is at least one material selected from silica, silicate, and aluminosilicate.
K. The process of embodiment I and J, wherein the inorganic support comprises silica.
L. The process of any one of embodiments I to K, wherein the second component comprises at least one metal component selected from platinum and palladium.
M. The process of any one of embodiments I to L wherein the first component comprises a metal component comprising potassium.
N. The process of any one of embodiments I to M, wherein the calcining (b) is conducted in an oxygen-containing atmosphere.
O. The process of any one of embodiments I to N, wherein the calcining (d) is conducted in an oxygen-containing atmosphere.
P. The process of any one of embodiments I to O, wherein the dehydrogenation conditions include a temperature of about 250° C. to about 500° C., a pressure of about 100 to 3550 kPa, a weight hourly space velocity of about 0.2 to 50 $hr^{-1}$, and a hydrogen to cyclohexanone-containing feed molar ratio of about 2 to about 20.
Q. The process of any one of embodiments I to P, wherein the effluent portion also comprises at least one compound selected from cyclohexanol, cyclohexenol, cyclohexenone and phenol.
R. The process of any one of embodiments I to Q and further comprising:
 (v) recycling at least part of the hydrogen produced in the contacting (iv) to the contacting (i).
S. A catalyst composition comprising: (i) a support; (ii) a first component comprising at least one metal component selected from Group 1 and Group 2 of the Periodic Table of Elements wherein the first component is present in an amount of at least 0.1 wt %; and (iii) a second component comprising at least one metal component selected from Groups 6 to 10 of the Periodic Table of Elements and wherein the catalyst composition has an oxygen chemisorption of greater than 50%.
T. The catalyst composition of embodiment S, wherein the catalyst composition has an oxygen chemisorption of greater than 60%.
U. The catalyst composition of embodiment S or T, wherein the catalyst composition has an oxygen chemisorption of greater than 70%.
V. The catalyst composition of any one of embodiments S to U, wherein the support is selected from the group consisting of silica, a silicate, an aluminosilicate, zirconia, carbon, and carbon nanotubes.
W. The catalyst composition of any one of embodiments S to V, wherein the support comprises silica.
X. The catalyst composition of any one of embodiments S to W, wherein the second component is at least one metal component selected from platinum and palladium.
Y. The catalyst composition of any one of embodiments S to X, wherein the second component is at least one metal component comprising platinum.
Z. The catalyst composition of any one of embodiments S to Y, wherein the first component is at least one metal component selected from potassium, cesium and rubidium.
AA. The catalyst composition of any one of embodiments S to Z, wherein the first component is at least one metal component comprising potassium.
BB. The catalyst composition of any one of embodiments S to AA, wherein the catalyst composition is capable of dehydrogenating cyclohexanone at a conversion of 95% or more.
CC. A method for preparing a catalyst composition, the method comprising:
 (a) treating a support with a first component comprising at least one metal component selected from Group 1 and Group 2 of the Periodic Table of Elements;
 (b) calcining the treated support at a temperature of about 100° C. to about 700° C.; and
 (c) impregnating the support with a second component comprising at least one metal component selected from Groups 6 to 10 of the Periodic Table of Elements, wherein the impregnating (c) is effected after or at the same time as the treating (a).
DD. The method of embodiment CC, wherein the calcining (b) is conducted in an oxygen-containing atmosphere.
EE. The method of embodiment CC or DD, wherein the impregnating (c) is affected after the treating (a) and the calcining (b).
FF. The method of any one of embodiments CC to EE, and further comprising:
 (d) calcining the impregnated support at a temperature of about 100° C. to about 600° C.
GG. The method of embodiment FF, wherein the calcining (d) is conducted in an oxygen-containing atmosphere.
HH. The method of embodiment FF, wherein the calcining (d) is conducted in an oxygen-containing atmosphere at a temperature of about 200° C. to about 500° C. for a time of about 1 to about 10 hours.
II. The method of embodiment FF, wherein the calcining (d) is conducted in an oxygen-containing atmosphere at a temperature of about 300° C. to about 450° C. for a time of about 1 to about 10 hours.
JJ. The method of any one of embodiments CC to II, wherein the support is selected from the group consisting of silica, a silicate, and an aluminosilicate.
KK. The method of any one of embodiments CC to JJ, wherein the support comprises silica.

LL. The method of any one embodiments CC to KK, wherein second component comprises at least one metal component selected from platinum and palladium.

MM. The method of any one of embodiments CC to LL, wherein the first component comprises at least one metal component comprising potassium.

The invention will now be more particularly described with reference to the following non-limiting examples and the accompanying drawing.

As used herein, the oxygen chemisorption value of a particular catalyst is a measure of metal dispersion on the catalyst and is defined as [the ratio of the number of moles of atomic oxygen sorbed by the catalyst to the number of moles of dehydrogenation metal contained by the catalyst]×100%. The oxygen chemisorption values referred to herein are measured using the following technique.

Oxygen chemisorption measurements are obtained using the Micromeritics ASAP 2010. Approximately 0.3 to 0.5 grams of catalyst are placed in the Micrometrics. Under flowing helium, the catalyst is ramped from ambient to 250° C. at a rate of 10° C. per minute and held for 5 minutes. After 5 minutes, the sample is placed under vacuum at 250° C. for 30 minutes. After 30 minutes of vacuum, the sample is cooled to 35° C. at 20° C. per minute and held for 5 minutes. The oxygen isotherm is collected at 35° C. in increments between 0.50 and 760 mm Hg.

EXAMPLE 1

1% K/1% Pt/SiO$_2$ (Sample A)

1 wt % platinum-containing 1/20" (1.3 mm) quadrulobe silica extrudate was prepared by incipient wetness impregnation using an aqueous solution of tetramine Pt nitrate. After impregnation, the sample was dried in air at 121° C., and the dried sample designated as 1% Pt/SiO$_2$. 1 wt % of K was loaded onto 1% Pt/SiO$_2$ by incipient wetness impregnation of a potassium carbonate solution. Following potassium impregnation, the sample was dried at 121° C. and then calcined at 350° C. in air for 3 hours. The sample is designated as 1% K/1% Pt/SiO$_2$. The oxygen chemisorption was measured as 48%.

EXAMPLE 2

1% Pt/1%/K/SiO$_2$ (Sample B)

A 1 wt % K containing 1/20" (1.3 mm) quadrulobe silica extrudate was prepared by incipient wetness impregnation using an aqueous solution of potassium carbonate solution. After K impregnation, the sample was dried in air at 121° C. followed by calcination in air at 538° C. for 3 hours. The calcined sample was designated as 1% K/SiO$_2$. 1 wt % of Pt was loaded onto 1% K/SiO$_2$ by incipient wetness impregnation of an aqueous solution of tetraamine platinum nitrate. Following platinum impregnation, the sample was dried at 121° C. and then calcined at 350° C. in air for 3 hours. The sample is designated as 1% Pt/1% K/SiO$_2$. The oxygen chemisorption was measured at 70%.

EXAMPLE 3

Performance Comparison of 1% K/1% Pt/SiO$_2$ with 1% Pt/1% K/SiO$_2$

Catalysts were cut into particles with L/D (length/diameter) of roughly 1 prior to catalyst testing. 600 mg of the catalyst was mixed with 3.5 g of about 40 mesh quartz chips, and the mixture was packed into a 3/8" (9.5 mm) stainless steel reactor. A thermocouple was inserted from the bottom of the reactor into the center of the roughly 5" (12.7 cm) catalyst bed for measuring catalyst bed temperature. Cyclohexanone feed was delivered at 9.5 ml/hr using an ISCO pump. Cyclohexanone feed was vaporized prior to mixing with 72 standard cubic centimeters per minute (sccm) of H$_2$. The mixture was fed into a downflow reactor. The reaction was typically run at 425° C. and 100 psig (689 kPag) total reactor pressure, so the cyclohexanone partial pressure was 37 psia (255 kPa-a). The weight hourly space velocity (WHSV) worked out to be about 15 hr$^{-1}$. The H2/cyclohexanone molar ratio of the feed was 2 to 1.

Prior to the introduction of cyclohexanone feed, the catalyst was pretreated in 72 sccm H$_2$ at 100 psig (689 kPag) by ramping reactor temperature from room temperature to 425° C. at 2° C./min; the reactor temperature was held at 425° C. for 3 hours under the same H$_2$ flow and pressure to allow for reduction of supported catalysts prior to testing.

The effluent from the reactor was sampled using a Valco sampling valve, and the sample was sent to an on-line GC equipped with a FID for analysis. All the hydrocarbons were analyzed and the results were normalized. H$_2$ was not included in the analysis. Conversion was calculated based on the concentration of cyclohexanone in the effluent. Cyclohexanol, which was typically present in the effluent, was counted as unreacted feed. All the concentrations shown here are in weight % (wt %).

The performance of the samples of Examples 1 and 2 in the dehydrogenation of cyclohexanone was tested in a fixed bed reactor at 425° C., 100 psig (791 kPa), 15 WHSV and H$_2$/cyclohexanone molar ratio of 2:1. FIG. 1 compares cyclohexanone conversion for the two catalysts and shows that the 1% Pt/1% K/SiO$_2$ of Example 2 is much more active than that of 1% K/1% Pt/SiO$_2$ of Example 1, consistent with the fact that the former shows much higher oxygen chemisorption than the latter.

EXAMPLE 4

0.5% Pt/1% K/SiO2 (Sample C)

A silica extrudate was impregnated using aqueous based incipient wetness impregnation with 1% K as potassium carbonate followed by air calcination at 540° C. After the potassium impregnation and calcination, the sample was impregnated with 0.5 wt % Pt using tetramine Pt nitrate solution using aqueous based incipient wetness impregnation. After impregnation, the extrudate was calcined in air at 250° C. The sample is designated as Sample C. The oxygen chemisorption was 82%.

EXAMPLE 5

0.5% Pt/1% K/SiO2 (Sample D)

A silica extrudate was impregnated using aqueous based incipient wetness impregnation with 1 wt % K as potassium carbonate followed by air calcination at 540° C. After the potassium impregnation and calcination, the sample was impregnated with 0.5 wt % Pt using tetramine Pt nitrate solution using aqueous based incipient wetness impregnation. After impregnation, the extrudate was calcined in air at 350° C. The sample is designated as Sample D. The oxygen chemisorption was 75%.

EXAMPLE 6

0.5% Pt/1% K/SiO2 (Sample E)

A silica extrudate was impregnated using aqueous based incipient wetness impregnation with 1% K as potassium carbonate followed by air calcination at 540° C. After the potassium impregnation and calcination, the sample was impregnated with 0.5 wt % Pt using tetraammine Pt nitrate solution using aqueous based incipient wetness impregnation. After impregnation, the extrudate was calcined in air at 500° C. The sample is designated as Sample E. The oxygen chemisorption was 61%.

EXAMPLE 7

1% Pt on a 1% K Silica Extrudate-Calcined 350° C.

A 1% K containing 1/20" (1.3 mm) quadrulobe extrudate was prepared by impregnating a silica extrudate with potassium carbonate (target 1% K) using incipient wetness impregnation. After impregnation, the extrudate was dried in air at 121° C. followed by calcination at 538° C. to convert the potassium carbonate to potassium oxide. A 1 wt % Pt containing 1/20" (1.3 mm) quadrulobe silica extrudate containing 1% K was prepared using tetraammine platinum hydroxide (target: 1 wt % Pt) solution using aqueous based incipient wetness impregnation. After impregnation, the extrudate was dried in air at 121° C. followed by air calcination at 350° C.

EXAMPLE 8

1% Pt on a 1% Ca Silica Extrudate-Calcined 350° C.

A 1% Ca containing 1/20" (1.3 mm) quadrulobe extrudate was prepared by impregnating a silica extrudate with calcium nitrate (target 1 wt % Ca) using incipient wetness impregnation. After impregnation, the extrudate was dried in air at 121° C. followed by calcination at 538° C. to convert the calcium nitrate to calcium oxide. A 1 wt % Pt containing 1/20" (1.3 mm) quadrulobe silica extrudate containing 1 wt % Ca was prepared using tetramine platinum hydroxide (target: 1 wt % Pt) solution using aqueous based incipient wetness impregnation. After impregnation, the extrudate was dried in air at 121° C. followed by air calcination at 350° C.

EXAMPLE 9

1% Pt on a 1% Mg Silica Extrudate-Calcined 350° C.

A 1 wt % Mg containing 1/20" (1.3 mm) quadrulobe extrudate was prepared by impregnating a silica extrudate with magnesium nitrate (target 1 wt % Mg) using incipient wetness impregnation. After impregnation, the extrudate was dried in air at 121° C. followed by calcination at 538° C. to convert the magnesium nitrate to magnesium oxide. A 1 wt % Pt containing 1/20" (1.3 mm) quadrulobe silica extrudate containing 1 wt % Mg was prepared using tetraammine platinum hydroxide (target: 1 wt % Pt) solution using aqueous based incipient wetness impregnation. After impregnation, the extrudate was dried in air at 121° C. followed by air calcination at 350° C. The oxygen chemisorption was measured at 53%.

EXAMPLE 10

Cyclohexanone Dehydrogenation to Phenol

The catalysts in Examples 7, 8, and 9 were evaluated for the conversion of cyclohexanone to phenol.

The reactor used in these experiments consists of a stainless steel tube with dimensions of 22 inches (56 cm) long×1/2 inch (12.7 mm) O.D.×0.035 inch (0.9 mm) wall thickness. A piece of stainless steel tubing 8¾ inches (22 cm) long×3/8 inches (9.5 mm) O.D. and a piece of ¼ inch (6.4 mm) tubing of similar length was used in the bottom of the reactor as a spacer (one inside the other) to position and support the catalyst in the isothermal zone of the furnace. A ¼" (6.4 mm) plug of glass wool was placed at the top of the spacer to keep the catalyst in place. A ⅛" (3.2 mm) stainless steel thermowell was placed in the cat bed, long enough to monitor temperature throughout the catalyst bed using a movable thermocouple.

The catalysts of Examples 7, 8, and 9 were crushed and sized to 20-40 US sieve mesh. Five grams of the catalyst in Examples 1, 2, and 3 were then loaded into the reactor from the top. The catalyst bed was typically 15 centimeters in length. A ¼ plug of glass wool was placed at the top of the catalyst bed to separate quartz chips from the catalyst. The remaining void space at the top of the reactor was filled with quartz chips. The reactor was installed in the furnace with the catalyst bed in the middle of the furnace at the pre marked isothermal zone. The reactor was then pressure tested at 300 psig (2068 kPag).

The catalysts of Examples 7, 8, and 9 were pre-conditioned in-situ by heating to 460° C. with hydrogen flow at 100 cc/min and held for two hours. A 500 cc Isco pump was used to introduce the cyclohexanone to the reactor. The feed was pumped through a vaporizer before flowing through heated lines to the reactor. A Brooks mass flow controller was used to maintain a constant hydrogen flow rate. A Grove "Mitey Mite" back pressure controller was used to maintain reactor pressure at 100 psig (689 kPag). The feed composition was verified by GC analysis. The feed was then pumped through the catalyst bed held at a reaction temperature of 425° C. at a WHSV of 2 and a pressure of 100 psig (689 kPag). The products exiting the reactor flowed through the heated lines to two collection pots in series. The non-condensable gas products were routed to an on-line HP 5890 GC. The first pot was heated to 60° C. and the second pot cooled with chilled coolant to 10° C. The product was collected at 12 and 24 hour intervals. Liquid samples were taken and diluted with 50% ethanol for GC analysis. A Hewlett Packard 6890 gas chromatograph with FID detector containing an Agilent technologies GC column 30 m×0.32 mm×0.25 micron film thickness was used for the analysis of the hydrocarbon products. The HP 6890 GC analysis ramp program was set to 40° C., ramped at 5° C./min to 150° C., then ramped at 10° C./min to 260° C. and held for 28 minutes. Total analysis time was 60 minutes.

Non-condensable gas products were analyzed using an on-line GC via a HP 5980 gas chromatograph with a J&W Scientific column 60 m×0.25 mm ID×1.0 micron film thickness. The HP 5980 GC ramp was set to 30° C. for 5 minutes, ramped at 5° C./min to 80° C. and held for 2 minutes, then ramped at 5° C./min to 200° C., then ramped at 5° C./min to 240° C. The total analysis time was 60 minutes.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for the dehydrogenation of at least one dehydrogenatable compound selected from a ketone and a hydrocarbon consisting of hydrogen and carbon, the process comprising contacting a feed comprising the at least one dehydrogenatable compound with a catalyst comprising an inorganic oxide support, a first component comprising at least one metal component selected from Group 1 and Group 2 of the Periodic Table of Elements, and a second component comprising at least one metal component selected from Groups 6 to 10 of the Periodic Table of Elements under dehydrogenation conditions effective to convert at least part of the at least one dehydrogenatable compound in the feed, wherein the catalyst is produced by a method comprising:
  (a) treating the support with the first component;
  (b) calcining the treated support at a temperature of about 100° C. to about 700° C.;
  (c) impregnating the support with the second component; and
  (d) calcining the impregnated support at a temperature of about 100° C. to about 700° C.,
wherein the impregnating (c) is effected after or at the same time as the treating (a).

2. The process of claim 1, wherein the inorganic support is at least one material selected from silica, a silicate, and an aluminosilicate.

3. The process of claim 1, wherein the inorganic support comprises silica.

4. The process of claim 1, wherein the second component comprises at least one metal component selected from platinum and palladium.

5. The process of claim 1, wherein the first component comprises a metal component comprising potassium.

6. The process of claim 1, wherein the calcining (b) is conducted in an oxygen-containing atmosphere.

7. The process of claim 1, wherein the calcining (d) is conducted in an oxygen-containing atmosphere.

8. The process of claim 1, wherein the dehydrogenation conditions include a temperature of about 250° C. to about 500° C., a pressure of about 100 to about 3550 kPa, a weight hourly space velocity of about 0.2 to 50 $hr^{-1}$, and a hydrogen to cyclohexanone-containing feed molar ratio of about 2 to about 20.

9. A process for producing phenol from benzene, the process comprising:
  (i) contacting benzene and hydrogen with a catalyst under hydroalkylation conditions to produce cyclohexylbenzene;
  (ii) oxidizing cyclohexylbenzene from the contacting (i) to produce cyclohexylbenzene hydroperoxide;
  (iii) converting cyclohexylbenzene hydroperoxide from the oxidizing (ii) to produce an effluent steam comprising phenol and cyclohexanone; and
  (iv) contacting at least a portion of the effluent stream with a catalyst comprising an inorganic oxide support, a first component comprising at least one metal component selected from Group 1 and Group 2 of the Periodic Table of Elements, and a second component comprising at least one metal component selected from Groups 6 to 10 of the Periodic Table of Elements under dehydrogenation conditions effective to convert at least part of the cyclohexanone in the feed into phenol and hydrogen, wherein the catalyst is produced by a method comprising:
  (a) treating the support with the first component;
  (b) calcining the treated support at a temperature of about 100° C. to about 700° C.;
  (c) impregnating the support with the second component; and
  (d) calcining the impregnated support at a temperature of about 100° C. to about 700° C.,
wherein the impregnating (c) is effected after or at the same time as the treating (a).

10. The process of claim 9, wherein the inorganic support is selected from at least one material selected from silica, a silicate, and an aluminosilicate.

11. The process of claim 9, wherein the inorganic support comprises silica.

12. The process of claim 9, wherein the second component comprises at least one metal component selected from platinum and palladium.

13. The process of claim 9, wherein the first component comprises a metal component comprising potassium.

14. The process of claim 9, wherein the calcining (b) is conducted in an oxygen-containing atmosphere.

15. The process of claim 9, wherein the calcining (d) is conducted in an oxygen-containing atmosphere.

16. The process of claim 9, wherein the dehydrogenation conditions include a temperature of about 250° C. to about 500° C., a pressure of about 100 to about 3550 kPa, a weight hourly space velocity of about 0.2 to about 50 $hr^{-1}$, and a hydrogen to cyclohexanone-containing feed molar ratio of about 2 to about 20.

17. The process of claim 9, wherein the effluent portion also comprises at least one compound selected from cyclohexanol, cyclohexenol, cyclohexenone and phenol.

18. The process of claim 9, and further comprising:
  (v) recycling at least part of the hydrogen produced in the contacting (iv) to the contacting (i).

19. The process of claim 1, wherein the at least one dehydrogenatable compound is selected from: cyclopropane, cyclopentane, methyl cyclopentane, cyclobutane, cyclopentene, cyclodecane, cyclohexane, methylcyclohexane, cyclododecane, cyclohexane, and cyclohexanone.

* * * * *